United States Patent [19]

Pollet et al.

[11] 4,072,523
[45] Feb. 7, 1978

[54] DEVELOPMENT OF PHOTOGRAPHIC SILVER HALIDE MATERIAL

[75] Inventors: Robert Joseph Pollet, Vremde; Francis Jeanne Sels, Kontich; Camille Angelina Vandeputte, Mortsel, all of Belgium

[73] Assignee: AGFA-GEVAERT, N.V., Mortsel, Belgium

[21] Appl. No.: 648,723

[22] Filed: Jan. 13, 1976

[30] Foreign Application Priority Data

Jan. 22, 1975  United Kingdom ............... 2867/75

[51] Int. Cl.$^2$ .................. G03C 5/30; G03C 1/48; G03C 7/00; G03C 7/16
[52] U.S. Cl. ............................. 96/22; 96/55; 96/66.3; 96/76 R; 96/95
[58] Field of Search ............ 96/66 R, 66.3, 107, 96/76, 95, 22, 55

[56] References Cited

U.S. PATENT DOCUMENTS

| B 417,498 | 3/1976 | Pollet et al. | 96/66 R |
|---|---|---|---|
| 3,021,215 | 2/1962 | Williams et al. | 96/107 |
| 3,046,134 | 7/1962 | Dann et al. | 96/107 |
| 3,523,797 | 8/1970 | Willems et al. | 96/66.3 |

*Primary Examiner*—Mary F. Kelley
*Attorney, Agent, or Firm*—A. W. Breiner

[57] ABSTRACT

A method is described of developing a photographic silver halide element containing developable silver halide by development in the presence of a development accelerator which is a compound corresponding to the following general formula and containing in its molecule at least one thioether sulphur atom linked to two carbon atoms:

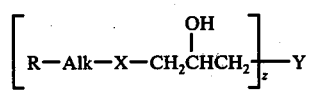

wherein:
R is hydrogen, hydroxy, hydroxyalkyl, alkoxy, alkylthio or alkylamino,
Alk is en alkylene group which may be interrupted by —O—, —S—, or —N(Q)— wherein Q is hydrogen or a $C_1$-$C_5$ alkyl group,
X is —O—, —S— or —N(Q)— wherein Q has the above meaning, and the value of z and the significance of Y are interdependent:
z being 1 for Y being hydroxy or the group —X'—Alk'—R' wherein
X', Alk' and R' have the same significance as X, Alk, and R,
z being 2 for Y being —O—, —S— or —N(Q)— wherein Q has the above meaning, and
z being a positive integer of at least 1 for Y being the residue of an aliphatic compound with more than one alcohol, thiol or amine function in which all or part of the alcohol-, thiol- or amine-hydrogen atoms are replaced by the group

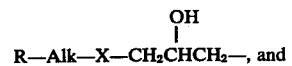

wherein the or at least one of the hydroxyl groups may have been converted into groups of the formula —OZA wherein Z is CO, $SO_2$ or CONH, and A is an alkyl or aryl group.

24 Claims, No Drawings

DEVELOPMENT OF PHOTOGRAPHIC SILVER HALIDE MATERIAL

The present invention relates to silver halide photography, and more particularly, to the development of photographic silver halide elements in the presence of compounds promoting the development.

It is known to increase the sensitivity of photographic emulsions by addition of chemical sensitizers e.g. sulphur-containing compounds, reducing agents and salts of gold or other noble metals or combinations of these compounds. Such chemical sensitizers are believed to react with the silver halide to form, on the surface of the silver halide, minute amounts of silver sulphide or of silver or of other noble metals which increases the sensitivity of the silver halide emulsion. This kind of chemical sensitization, however, reaches a limit beyond which further addition of sensitizer or further digestion with the sensitizer merely increases the fog of the emulsion with constant or decreasing speed.

As is known in the art, further increasing of the speed of the photographic reproduction system can be effected by the presence during development of alkylene oxide polymers, e.g. polyoxyethylene compounds, thioether compounds and/or onium or polyonium compounds of the ammonium, phosphonium or sulphonium type. These compounds sensitize the emulsion by development acceleration and may be used either in the emulsion or the developer.

We have now found that development of exposed silver halide emulsions can be activated by the presence during development e.g. in the developer or in the photographic element, of a compound corresponding to the following general formula I and containing in its molecule at least one thioether group i.e. a divalent sulphur atom joined to two carbon atoms:

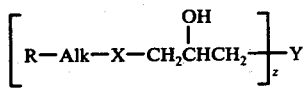   I wherein:

R is hydrogen, hydroxy, hydroxyalkyl, alkoxy, alkylthio or alkylamino; the alkyl groups comprising preferably at most 5 C-atoms.

Alk is an alkylene group which may be interrupted by —O—, —S— and —N(Q)— wherein Q is hydrogen or, preferably, $C_1$–$C_5$ alkyl which may be substituted e.g. by hydroxy, alkoxy or alkylthio.

X is —O—, —S— or —N(Q)— wherein Q has one of the significances given;

the value of z and the significance of Y are interdependent:

z being 1 for Y being hydroxy or the group —X'—Alk'—R' wherein X', Alk' and R' have one of the significances given for X, Alk and R, z being 2 for Y being —O—, —S— or —N(Q)— wherein Q has one of the significances given, z being a positive integer of at least 1 for Y being the residue of an aliphatic compound with more than one alchol, thiol or amine function in which all or part of the alcohol, thiol or amine hydrogen atoms are replaced by the group

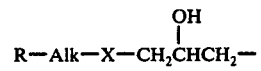

e.g. the residue of an aliphatic diol, polyol, dithiol, polythiol, diamine, polyamine, mercapto-alcohol, aminoalcohol and mercapto-amine, which may be interrupted by O, S, or N(Q) wherein Q is as defined above, or a compound of the above general formula I wherein the hydroxyl group or at least one of the hydroxyl groups has been converted into groups of the formula —OZA, wherein Z is CO, $SO_2$ or CONH, and A is alkyl including substituted alkyl or aryl including substituted aryl, e.g.

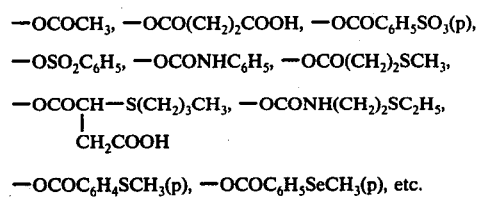

The above development accelerators may be used for various kinds of photographic silver halide elements. They can be used in the black-and-white development as well as the colour development of photographic silver halide elements. They are useful for negative development but are preferably used for reversal development.

The present invention thus provides a method of developing a photographic element containing developable silver halide in the presence of a compound as defined above. The present invention also provides a silver halide developing composition containing a silver halide developing agent and a compound as defined above.

One group of compounds falling within the scope of formula I above, which can be employed in the present invention, comprises compounds represented by the following general formula II:

   II wherein each of $Y_1$ and $Y_1'$, which are preferably the same but may be different, is O, S, or N(Q) wherein Q is hydrogen, or preferably $C_1$–$C_5$ alkyl which may be substituted e.g. by hydroxy, alkoxy and alkylthio, n is 0 or 1, alkylene stands for an alkylene group which may be interrupted by O, S, or N(Q) wherein Q stands for hydrogen, or preferably $C_1$–$C_5$ alkyl which may be substituted e.g. by hydroxy, alkoxy, alkylthio, each of $X_1$ and $X_1'$, which may be the same or different, stands for O, S or N(Q) wherein Q is hydrogen or preferably, $C_1$–$C_5$ alkyl which may be substituted e.g. by hydroxy, alkoxy, alkylthio, each of $Alk_1$ and $Alk_1'$, which may be the same or different, stands for alkylene, preferably $C_1$–$C_5$ alkylene, which may be interrupted by O, S, or N(Q) wherein Q has the meaning given, each of $R_1$ and $R_1'$, which may be the same or different, stands for hydrogen, hydroxy, hydroxyalkyl, alkoxy, alkylthio, or alkylamino the alkyl groups comprising at most 5 C-atoms, and wherein at least one thioether S-atom is present in the molecule: $X_1$, $X_1'$, $Y_1'$ or in $R_1$, $R_1'$, $Alk_1$, $Alk_1'$ or alkylene.

Another group of compounds falling within the scope of formula I above which can be employed in the present invention, comprises compounds represented by the following general formulae III and IV:

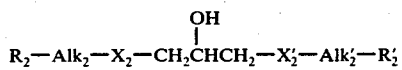

$$R_2-Alk_2-X_2-CH_2\overset{\underset{\mid}{OH}}{C}HCH_2-X_2'-Alk_2'-R_2' \qquad III$$

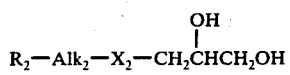

$$R_2-Alk_2-X_2-CH_2\overset{\underset{\mid}{OH}}{C}HCH_2OH \qquad IV$$

wherein
each of $R_2$ and $R_2'$, which may be the same or different, stands for hydrogen, hydroxy, hydroxyalkyl, alkoxy, alkylthio or alkylamino, the alkyl groups comprising preferably at most 5 C-atoms, each of $Alk_2$ and $Alk_2'$, which may be the same or different, stands for alkylene, preferably $C_1$-$C_5$ alkylene which may be interrupted by O, S or N(Q), wherein Q is hydrogen or, preferably $C_1$-$C_5$ alkyl which may be substituted e.g. by hydroxy, alkoxy, alkylthio, and each of $X_2$ and $X_2'$, which may be the same or different, stands for O, S or N(Q), and wherein at least one thioether S-atom is present in the molecule; preferably $X_2$, $X_2'$, or in $R_2$, in $R_2'$, in $Alk_2$ or in $Alk_2'$.

A further group of compounds falling within the scope of formula I above, which can be employed in the present invention, comprises compounds represented by the following general formula V:

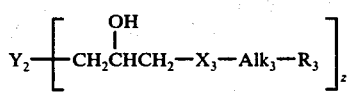

$$Y_2\left[-CH_2\overset{\underset{\mid}{OH}}{C}HCH_2-X_3-Alk_3-R_3\right]_z \qquad V$$

wherein
$Y_2$ is the residue of a polyhydric alcohol containing at least 3 hydroxyl groups e.g. glycerol, pentaerythritol, mannitol, sorbitol and glucose wherein at least one and preferably substantially all alcohol hydrogen atoms have been replaced by the group between brackets, z is an integer of at least 1, $X_3$ is O, S, or N(Q) wherein Q is hydrogen, preferably $C_1$-$C_5$ alkyl which may be substituted e.g. by hydroxyl, alkoxy, alkylthio, $Alk_3$ stands for a $C_1$-$C_5$ alkylene group, and $R_3$ is hydrogen, hydroxy, hydroxyalkyl, alkoxy, alkylthio or alkylamine, the alkyl groups preferably comprising at most 5 C-atoms, and wherein at least one of $X_3$, $Alk_3$ and $R_3$ is or comprises a thioether S-atom.

Compounds represented by the above formula I to V can be prepared according to various methods. They can be prepared e.g.

by reacting a bisepoxide with an aliphatic, optionally substituted alcohol, thiol or amine, preferably secondary amine, by first reacting an aliphatic alcohol, thiol or amine with epichlorohydrin and then further reacting the compound obtained with an aliphatic alcohol, thiol or amine or an aliphatic compound comprising several alcohol, thiol or amine functions, or vice versa, and by reacting 3-chloro(bromo)-1,2-propane diol with a thiol or amine or an aliphatic compound comprising several thiol or amine functions.

The compounds corresponding to the above general formula comprise at least one thioether S-atom which means that in the above reactions at least one of reactants comprises a thioether S-atom or is a thiol.

Examples of bisepoxides for reaction with alcohols, thiols or amines to form compounds of the above general formula are:

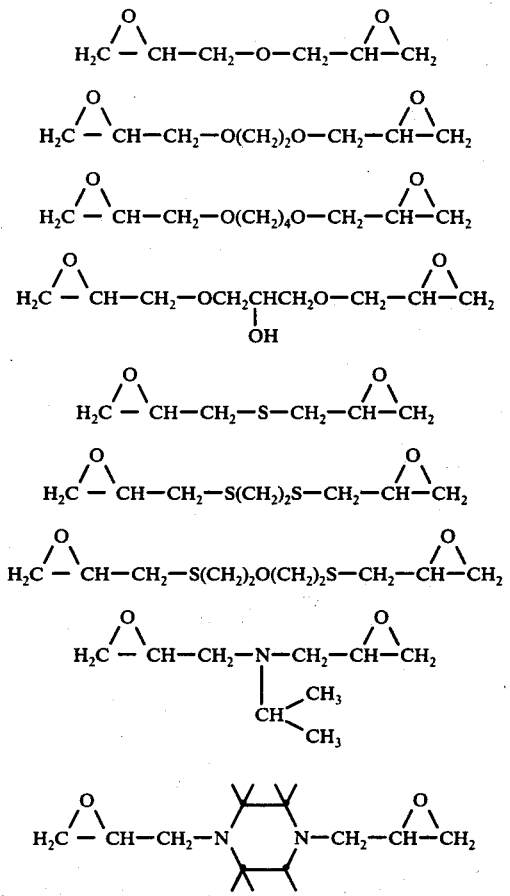

Examples of alcohols, thiols, amines and compounds containing more than one alcohol, thiol or amine function for use in the above reactions are: ethanol, β-ethylthio ethanol, ethane thiol, 2-mercapto-ethanol, 3-mercapto-1,2-propane diol, ethylamine, diethylamine, β-ethylthioethylamine, ethane diol (ethylene glycol), propane diol, trimethylol propane, polyethylene glycol, polyethylene glycol monomethyl ether, glycerol, pentaerythritol, mannitol, sorbitol, glycose, ethane dithiol, propanetrithiol, 3-thia-1,5-pentane diol, 3,6-dithia-1,8-octane diol, 3,7-dithia-1,9-nonane diol, 4,7-dithia-1,10-decane diol, 3-ethylthio-1,2-propane diol, ethylene diamine, diethylene triamine, thriethylene tetraamine, N-β-hydroxyethyl-ethanolamine, bis(2-aminoethyl)sulphide, 3-oxa-1,5-pentane dithiol, 3,6-dioxa-1,8-octane thiol, etc.

Specific examples of compounds corresponding to the above general formulae are:
1. 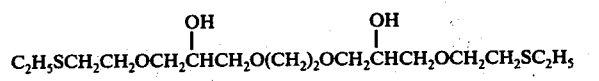
2. 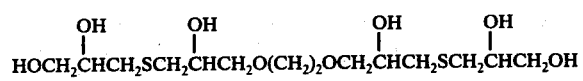
3. 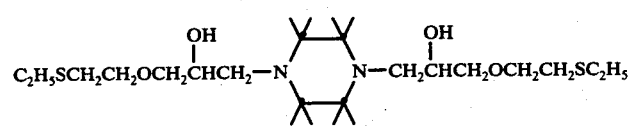
4. 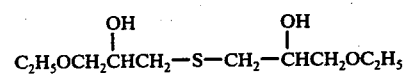
5. 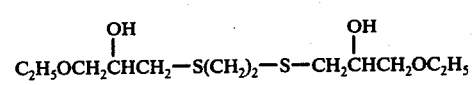
6. 
7. 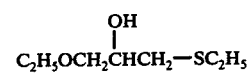
8. 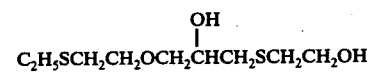
9. 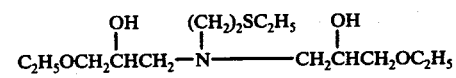
10. 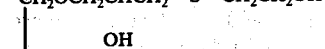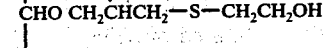
11. 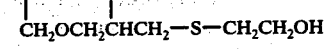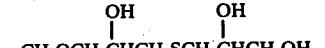
12. 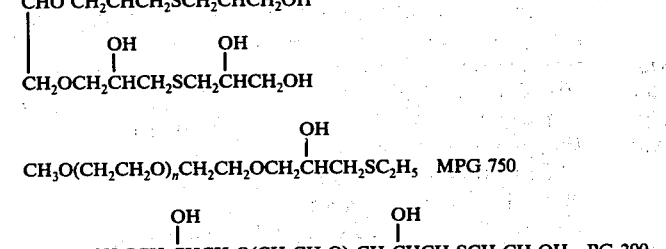
13. 
14. 
15. 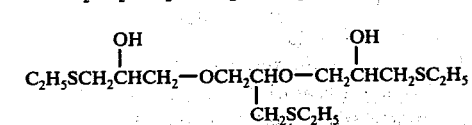

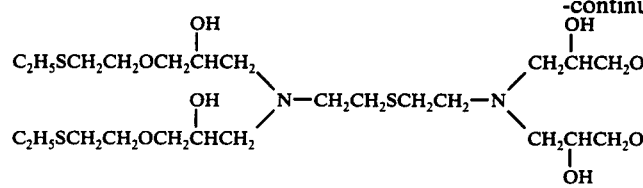 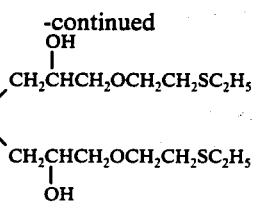

16.

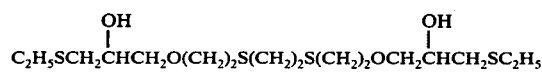

17.

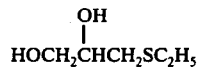

18.

19.

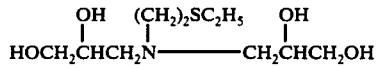

20.

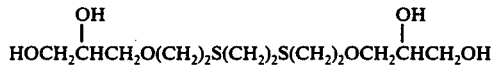

21.

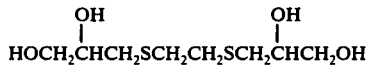

22.

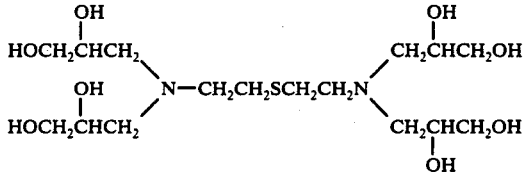

23.

The above compounds can be prepared as described hereinbefore and as illustrated by means of the preparations hereinafter.

Terminal hydroxyl groups of the compounds corresponding to the above general formulae can be converted into -OZA groups wherein Z and A are defined as hereinbefore by reaction with the appropriate carboxylic or sulphonic acid chloride, acid anhydride or isocyanate.

Preparation 1 : compound 1

A mixture of 31.8 g of β-ethylthioethanol, 26.1 g of ethylene glycoldiglycidether and a catalytic amount of potassium hydroxide was heated under nitrogen atmosphere for 20 hours at 105° C. The volatile substances were distilled off under reduced pressure (10 mm Hg) at a temperature of 100° C for 6 hours.

Yield: 48 g.

Preparation 2: compound 2

To a mixture of 32.4 g of thioglycerol and a catalytic amount of sodium methylate heated to 60° C and under nitrogen atmosphere, 26 g of ethylene glycol diglycidether were added dropwise. The mixture was heated for 8 hours at 105° C.

Yield: 57 g.

Preparation 3: compound 3

29.7 g of 1.4-bis(2,3-epoxy propyl)piperazine were added dropwise to a mixture of 31.8 g of ethylthioethanol and a catalytic amount pf potassium hydroxide, heated to 100° C and under nitrogen atmosphere. Then, the mixture was heated first for 20 hours at a temperature of 100° C and subsequently for 8 hours at 130° C.

Yield: 61 g.

Preparation 4: compound 10

46.8 g of mercapto ethanol were added at room temperature to a solution of 13.8 of sodium in 500 ml of ethanol. Then a solution of 73.9 g of tris(3-chloro-2-hydroxy propyl)-glycerine in 400 ml of ethanol were added. The mixture was boiled for 8 hours and a precipitate of sodium chloride formed gradually. The mixture was cooled and the precipitate filtered off. The filtrate was concentrated by evaporation and a viscous oil was obtained.

Yield: 99 g.

Preparation 5: compound 18

To a solution of 11.5 g of sodium in 500 ml of dry ethanol, 54 g of thioglycerol were added at room temperature followed by dropwise addition of 81 g of bromoethane. A white precipitate forms gradually. The mixture was boiled for 4 hours whereupon the white precipitate was filtered off and the filtrate concentrated by evaporation. The residue was distilled. Boiling point: 101° C (1 mm Hg).

Yield: 46 g.

Preparation 6: compound 19

To a solution of 11.5 g of sodium in 500 ml of dry ethanol, 39 g of mercaptoethanol were added at room temperature. Then, 55 g of 3-chloro-1,2-dihydroxy propane were added dropwise at room temperature. The mixture was boiled for 7 hours and the white precipitate filtered off. The filtrate was concentrated by evaporation.

Yield: 74.5 g.

Preparation 7: compound 23

To a solution of 40 g of diaminodiethylsulphide in 100 ml of dry dioxan, a solution of 98.5 g of glycidol in 200 ml of dioxan was added dropwise at a temperature of 50° C. A thick slimy product was formed. The solvent was decanted and the residue was evaporated under reduced pressure until dry.

Yield: 138 g.

The development accelerators of the present invention may be used in the photographic silver halide material but they are preferably incorporated in the developer composition comprising black-and-white developing agents e.g. hydroquinone, hydroquinone/1-phenyl-3-pyrazolidinone, hydroquinone/p-monomethylaminophenol sulphate or colour developing agents more particularly aromatic primary amino colour developing agents e.g. p-phenylene diamine colour developing agents. The compounds are particularly suitable for use in colour developing compositions.

The development accelerating compounds can be utilized in various concentrations, depending upon the effects desired, the particular silver halide emulsions employed, the thickness of the emulsion layers, the concentration of silver halides in the emulsions, the concentration of developing agents in the developers, the pH of the developers etc. The optimum amount for any given compound can be determined for any particular emulsion or developer by running a series of tests in which the quantity is varied over a certain range.

In general, useful results are obtained when the concentration of the thioether compound in the developer is from about 50 mg to about 10 g per litre. The activity of the developer will obviously depend upon the temperature of development, which may be room temperature or elevated temperature e.g. above 30° C, upon the duration of development and the like.

When incorporated in the emulsion, the compounds are generally used in concentrations varying from about 10 mg to about 5 g per mole of silver halide. They can be added to the emulsion in no matter what step of emulsion preparation, preferably, however, just before coating.

The above thioether development accelerators can be added to the emulsion or developer using any technique e.g. from a solution or dispersion in a suitable solvent. Of course the solvents used should have no harmful effect on the emulsion and generally solvents which are miscible with water are to be preferred. For example the thioether compounds can be dissolved in water or solvents such as ethanol, acetone, pyridine, N,N-dimethylformamide, dimethyl sulphoxide, N-methylpyrrolidone, etc.

If desired, the compounds of the present invention can be treated with various alkylating agents e.g. the esters of an alcohol and a strong acid such as methyl or ethyl esters of sulphuric acid, phosphoric acid, hydrpchloric acid, hydrobromic acid, hydroiodic acid, benzene sulphonic acid, p-toluene sulphonic acid, etc. to convert at least one thioether S-atom into a sulphonium atom. In general, it suffices to merely heat the thioether compound with the alkylating agent. By the presence of the ternarized sulphonium atoms, improved solubility in water or various water-miscible solvents is obtained.

The silver halide emulsions which are developed in the presence of the thioether compounds defined above, comprise as light-sensitive silver halide, silver bromide, silver iodide, silver chloride or mixed silver halides e.g. silver chlorobromide, silver chlorobromoiodide or silver bromoiodide. The emulsions can be chemically sensitized by any of the accepted procedures. The emulsions can be digested with naturally active gelatin or with sulphur-containing compounds e.g. allyl isothiocyanate, allyl thiourea or sodium thiosulphate. The emulsion can also be digested in the presence or reducing agents e.g. the tin compounds described in Belgian Patent Specifications 493,464 and 568,687, the iminoaminomethane sulphinic acid compounds described in United Kingdom Patent Specification 789,823, polyamines e.g. diethylene triamine, spermine and bis($\beta$-aminoethyl) sulphide. They can further be digested in the presence of noble metal compounds such as ruthenium, rhodium, palladium, iridium, platinum and gold compounds as described by R.Koslowsky, Z.Wiss.Phot. 46, 65-72 (1951). Representative compounds are ammonium chloropalladate, potassium chloroplatinate, sodium chloropalladite, potassium chloroaurite, potassium aurithiocynate, potassium chloroaurate, gold(III) chloride, gold(I) sulphide, etc.

The emulsions can comprise emulsion-stabilizers and fog-inhibiting compounds e.g. the mercury compounds such as those described in Belgian Patent Specifications 524,121 and 677,337 and in published Dutch Patent Application 67/15932, organic sulphur-containing compounds that form insoluble silver salts with silver ions, heterocyclic nitrogen-containing thioxo compounds or derivatives thereof, e.g. benzothiazoline-2-thione, 1-phenyl-2-tetrazoline-5-thione and 2-ethoxycarbonylthio-5-amino-thiadiazole, the compounds described in Belgian Patent Specifications 571,916 and 571,917, thiazolinium compounds of the type described in Product Licensing Index, December 1971 issue, p. 90–91, benzothiazolium compounds e.g. 2,3-dimethyl-5-methoxycarbonyl benzthiazolium p-toluene sulphonite and tetra- or pentaazaindenes especially those substituted by hydroxyl or amino groups e.g. those described by Birr, Z.Wiss.Phot. 47, 2-58 (1952). A very effective azaindene emulsion stabilizer in 5-methyl-7-hydroxy-s-triazolo[1,5-a]pyrimidine which can be used together with other emulsion stabilizers e.g. those of the type described above.

The emulsions may be X-ray and other non-spectrally sensitized emulsions as well as orthochromatic, panchromatic or infrared-sensitive emulsions. The emulsions may be spectrally sensitized by means of neutrocyanines, carboxycyanines, rhodacyanines, hemicyanines, merocyanines, oxonol dyes, styryl dyes and the like as described by F. M. Hamer in "The cyanine dyes and related compounds" (1954).

The emulsions may further comprise other compounds that sensitize the emulsion by development acceleration e.g. alkylene oxide polymers. These alkylene oxide polymers may be of various type e.g. polyethylene glycol having a molecular weight of 1500 or more, alkylene oxide condensation products or polymers as described in U.S. Pat. Specifications 1,970,578 – 2,240,472 – 2,423,549 – 2,441,389 – 2,531,832 and 2,533,990 and in United Kingdom Patent Specification Nos. 920,637 – 940,051 – 945,340 – 991,608 and 1,015,023. These development accelerating compounds may also be present in the silver halide developing solution. Other development accelerating compounds are onium and polyonium compounds preferably of the ammonium, phosphonium and sulphonium type.

Other addenda e.g. hardening agents such as formaldehyde, mucochloric and mucobromic acid, dialdehydes, etc., wetting agents, plasticizers, matting agents, e.g. polymethyl methacrylate and silica particles, light-screening dyes, etc., may be present in the silver halide emulsion or another layer of the light-sensitive materials used according to the invention.

The compounds of the present invention may be used for various kinds of photographic silver halide elements e.g. black-and-white emulsions which include X-ray and lith emulsions and colour emulsions. They may be used in the silver complex diffusion transfer process and in addition to being useful for negative processing they may also be used for reversal processing. In reversal processing where after a first black-and-white development residual silver halide is rendered developable by uniform reexposure or by a chemical treatment and then developed by a second development which may be black-and-white or colour, the compounds of the invention are preferably used in the second developer so that development of the residual silver halide rendered developable is activated and thus maximum density is increased.

The thioether compounds of the present invention have been found particularly useful for the development, especially reversal development, of photographic colour emulsions. They can be used in the production of multicolour images as well as in the production of monochromic images e.g. monochromic radiographic dye images according to the technique described in U.S. Pat. No. 3,734,735 and U.S. Pat. Application Ser. No. 210,566 (= published German Pat. Application 2,165,193). They can also be used in colour diffusion transfer processes.

As is known in the art of silver halide colour photography, dyestuff images are formed by coupling of appropriate colour forming couplers with the oxidation products of aromatic primary amino colour developers particularly p-phenylene diamine colour developing agents. By the presence during the colour development of the novel accelerators, the maximum density of the dyestuff images as well as the contrast can be increased which results in improved colour saturation. Moreover, in addition to having a favourable development accelerating action, these compounds do not give rise to difficulties in the subsequent bleaching of the silver image as often occurs when using development accelerating onium compounds e.g. quaternary ammonium compounds.

In multilayer photographic elements used in colour photography for the reproduction of multicolour images there are generally three selectively sensitive emulsion layers (each of which may consist of several strata finished to different speed levels) coated on the same side of a photographic support, such as film or paper. Such multilayer elements can also have other layers for special purposes including gelatin or other subbing layers, antihalation layers, protective coatings, etc.

The three selectively sensitive emulsion layers are a blue-sensitive emulsion layer, an emulsion layer sensitized to the green region of the spectrum and an emulsion layer sensitized to the red region of the spectrum. In as much as many photographic silver halide emulsions have an inherent blue sensitivity, the photographic elements generally have a yellow filter layer beneath the blue-sensitive uppermost emulsion layer for the purpose of absorbing substantially all blue radiation which would otherwise be transmitted to the green- and red-sensitized emulsion layers.

Though the invention is primarily concerned with colour materials comprising the colour-forming couplers within the silver halide emulsions, the materials may also be of the type well known in the art and designed for processing in developers which contain the colour forming couplers within the colour developer.

The colour-forming couplers are of the customary types employed in colour photography: pyrazolone couplers for formation of the magenta image, phenolic or naphtholic couplers for formation of the cyan image and open-chain compounds containing a reactive methylene group for formation pf the yellow image.

When the multicolour elements have incorporated colour couplers the blue-sensitive emulsion layer comprises the yellow-forming colour coupler, the green-sensitized emulsion layer comprises the magenta-forming colour coupler and the red sensitized emulsion layer comprises the cyan-forming colour coupler.

For the incorporation of the colour forming couplers in the silver halide emulsions, the conventional methods can be applied, e.g. they can be incorporated from solutions in high-boiling sparingly water-miscible solvents such as di-n-butyl phthalate and tricresyl phosphate or in lowboiling sparingly water-miscible solvents such as ethyl acetate, methylene chloride and chloroform, etc. or mixtures of both types of solvents. For this purpose these solutions are dispersed in extremely fine droplets, preferably in the presence of a wetting or dispersing agent into the hydrophilic colloid medium, the low-boiling sparingly water-miscible solvent then being removed by evaporation. Of course other techniques known by those skilled in the art for incorporating colour couplers, into colloid compositions can be used. For instance, the water-soluble colour couplers i.e. those containing a water-solubilizing sulpho group, in acid or salt form, can be incorporated into the coating composition of the layer in question from an aqueous or alkaline solution.

The hydrophilic colloid composition into which the colour couplers are dispersed or dissolved need not necessarily be the coating composition itself of the silver halide emulsion layer into which the colour couplers are intended to be present. The compounds may advantageously be first dispersed or dissolved in an aqueous non-light-sensitive hydrophilic colloid solution whereupon the resultant mixture after the occasional removal of the organic solvents employed, is intimately mixed with the said coating composition of the light-sensitive silver halide emulsion layer just before coating.

For more details about particularly suitable techniques that may be employed for incorporating colour couplers into a silver halide emulsion layer of a photographic material there can be referred to e.g. U.S. Pat. Nos. 2,269,158 - 2,284,887 - 2,304,939 - 2,304,940 and 2,322,027, United Kingdom Patent Specifications 791,219 - 1,098,594 - 1,099,414 - 1,099,415 - 1,099,416 and 1,099,417, French Patent Specification 1,555,663, Belgian Patent Specification 722,026, German Patent Specification 1,127,714 and to United Kingdom Patent Application 14,763/69.

In the colour development aromatic primary amino developing substances are used, which are capable of forming azomethine dyes by coupling in their oxidized form with the colour-forming couplers. Suitable developing agents are more particularly p-phenylene diamine and derivatives thereof e.g. N,N-dialkyl-p-phenylene diamines, N,N-dialkyl-N'-sulphomethyl-p-phenylenediamine, N,N-dialkyl-N'-carboxymethyl-p-phenylenediamine, the sulphonamido substituted p-phenylene diamines disclosed in U.S. Pat. No. 2,548,574 and other substituted p-phenylene diamines disclosed in U.S. Pat. No. 2,566,271.

Typical examples of p-phenylenediamines are N,N-diethyl p-phenylene diamine, 2-amino-5-diethylaminotoluene, N-butyl-N-sulphobutyl-p-phenylene diamine, 2-amino-5-[N-ethyl-N(α-methylsulphonamido)ethyl]aminotoluene, N-ethyl-N-β-hydroxyethyl-p-phenylenediamine, etc. These developing agents are used usually in their salt form such as the hydrochloride or sulphate.

The following examples illustrate the present invention.

EXAMPLE 1

Strips of a conventional multicolour reversal film material containing incorporated colour couplers for the cyan, magenta and yellow separation images were exposed through a grey continuous wedge to white light in a Herrnfeld Sensitometer.

The exposed strips were then processed as follows: treatment for 10 seconds at 25° C in a pre-bath of the following composition:

| | |
|---|---|
| water | 800 ml |
| ethylene diamine tetraacetic acid tetrasodium salt | 2 g |
| anhydrous sodium sulphate | 100 g |
| borax | 15 g |
| water to make | 1000 ml |
| | (pH 9.30) | rinsing for 15 seconds and brushing of the back to remove antihalation layer;
developing for 3 min. 45 sec. at 25° C in a black-and-white developer of the following composition:

| | |
|---|---|
| N-methyl-p-aminophenol sulphate | 3 g |
| hydroquinone | 6 g |
| sodium metabisulphite | 0.5 g |
| sodium hexametaphosphate | 2 g |
| sodium sulphite | 50 g |
| anhydrous sodium carbonate | 40 g |
| potassium bromide | 2.3 g |
| potassium thiocyanate | 2.5 g |
| potassium iodide | 6 mg |
| water to make | 1000 ml |
| | (pH 10.2) | treatment for 2 minutes in a stop bath of the following composition:

| | |
|---|---|
| potassium alum | 15 g |
| boric acid | 6 g |
| sodium hydrogen diacetate | 15 g |
| sodium metabisulphite | 1 g |
| water to make | 1000 ml |
| | (pH 4.2) | rinsing with water for 3 minutes and overall re-exposing the material for 1 minute at 25° C;
colour developing for 4 minutes at 25° C in a colour developer of the following composition:

| | |
|---|---|
| sodium hexametaphosphate | 1 g |
| sodium sulphite | 4 g |
| anhydrous sodium carbonate | 25 g |
| potassium bromide | 2.2 g |
| sodium hydroxide | 0.6 g |
| hydroxylamine hydrochloride | 1.2 g |
| N,N-diethyl-p-phenylene diamine hydrochloride | 2.7 g |
| potassium iodide | 4 mg |
| development activator as listed in the table hereinafter | 250 mg |
| water to make | 1000 ml |
| | (pH 10.7) | rinsing with water for 10 sec. at 25° C;
fixing for 3 minutes at 25° C in the following fixing solution:

| | |
|---|---|
| potassium alum | 15 g |
| acid sodium sulphate | 13 g |
| sodium acetate trihydrate | 25 g |
| sodium bisulphite | 12 g |
| sodium thiosulphate | 200 g |
| water to make | 1000 ml |
| | (pH 3.9) | rinsing with water for 2 min. at 25° C;
silver bleaching for 4 min. at 25° C in the following bleach bath:

| | |
|---|---|
| potassium bromide | 15 g |
| potassium alum | 45 g |
| acid potassium sulphate | 2 g |
| sodium acetate trihydrate | 5 g |
| sodium hydrogen diacetate | 10 g |
| potassium hexacyanoferrate(III) | 75 g |
| water to make | 1000 ml |
| | (pH 3.9) | rinsing with water for 3 min. at 25° C;
treating for 3 min. at 25° C in the above fixing solution,
rinsing with water for 5 min. at 25° C, and
stabilizing for 8 sec. at 25° C in a stabilizing bath comprising per liter 13 ml of a 40% aqueous formaldehyde solution and a wetting agent.

In the following table the values are given which were obtained for minimum and maximum density and for the average gradient of the characteristic curves measured over an exposure range of Δ log It = 0.60 beginning at the point corresponding to density 0.70 above fog.

Table

| Development activator | $D_{min}$ | | | $D_{max}$ | | | Gradient | | |
|---|---|---|---|---|---|---|---|---|---|
| | blue | green | red | blue | green | red | blue | green | red |
| none | 0.23 | 0.15 | 0.14 | 1.69 | 1.75 | 1.50 | 0.86 | 0.91 | 1.07 |
| 2 | 0.17 | 0.09 | 0.09 | 1.85 | 1.76 | 1.94 | 1.03 | 0.95 | 1.23 |
| 3 | 0.20 | 0.11 | 0.11 | 2.41 | 2.24 | 2.23 | 1.61 | 1.43 | 1.73 |
| 18 | 0.20 | 0.13 | 0.14 | 1.80 | 1.72 | 1.66 | 1.03 | 0.92 | 1.01 |

The above results show that when colour development takes place in the presence of a compound according to the present invention, higher constrast and higher maximum density are obtained. The selectivity of colour reproduction is also favourable.

EXAMPLE 2

This example is analogous to example 1 with the only difference that another conventional multicolour reversal material was used and the amount of development accelerator used was 2 g/liter.

| Development | $D_{min}$ | | | $D_{max}$ | | | Gradient | | |
| --- | --- | --- | --- | --- | --- | --- | --- | --- | --- |
| accelerator | blue | green | red | blue | green | red | blue | green | red |
| none | 0.12 | 0.10 | 0.05 | 1.33 | 1.51 | 1.60 | 0.72 | 0.89 | 1.06 |
| 1 | 0.10 | 0.08 | 0.06 | 2.37 | 2.55 | 2.88 | 1.70 | 1.64 | 1.91 |
| 10 | 0.16 | 0.10 | 0.07 | 2.05 | 2.34 | 2.77 | 1.44 | 1.63 | 1.87 |
| 11 | 0.10 | 0.67 | 0.03 | 1.56 | 1.85 | 2.39 | 1.01 | 1.16 | 1.47 |

We claim:
1. A method of developing a photographic element containing imagewise developable silver halide wherein development occurs in the presence of a compound, incorporated in the element or in the developer, corresponding to the following general formula and containing in its molecule at least one thioether sulphur atom linked to two carbon atoms:

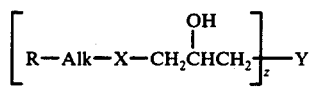

wherein:
R is hydrogen, hydroxy, hydroxyalkyl, alkoxy, alkylthio or alkylamino,
Alk is an alkylene group which may be interrupted by —O—, —S—, or —N(Q)— wherein Q is hydrogen or a $C_1$-$C_5$ alkyl group,
X is —O—, —S— or —N(Q)— wherein Q has the above meaning, and the value of z and the significance of Y are interdependent:
z being 1 for Y being hydroxy or the group —X'—Alk'—R' wherein X', Alk' and R' have the same significance as X, Alk and R,
z being 2 for Y being —O—, —S— or —N(Q)— wherein Q has the above meaning, and
z being a positive integer of at least 1 for Y being the residue of an aliphatic compound with more than one alcohol, thiol or amine function in which all or part of the alcohol-, thiol-, or amine-hydrogen atoms are replaced by the group

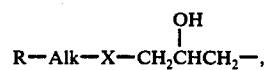

and
wherein the or at least one of the hydroxyl groups may have been converted into groups of the formula —OZA wherein Z is CO, $SO_2$ or CONH, and A is an alkyl or aryl group and wherein at least one of R, Alk, X and Y is or includes a thioether sulphur atom.
2. A method according to claim 1, wherein the compound corresponds to the formula:

wherein:
each of $Y_1$ and $Y_1'$ represents —O—, —S— or —N(Q)— wherein Q is hydrogen or a $C_1$-$C_5$ alkyl group,
n is 0 or 1,
alkylene is an alkylene group which may be interrupted by —O—, —S— or —N(Q)— wherein Q is as defined above,
each of $X_1$ and $X_1'$ represents —O—, —S— or —N(Q)— wherein Q is as defined above,
each of $Alk_1$ and $Alk_1'$ is an alkylene group which may be interrupted by —O—, —S— or —N(Q)— wherein Q is as defined above, and
each of $R_1$ and $R_1'$ stands for hydrogen, hydroxy, hydroxyalkyl, alkoxy, alkylthio or alkylamino;
and wherein at least one of $R_1$, $Alk_1$, $X_1$, $R_1'$, $Alk_1'$, $X_1'$, $Y_1$, $Y_1'$ or alkylene is or comprises a thioether sulphur atom.
3. A method according to claim 1, wherein the compound corresponds to one of the formulae:

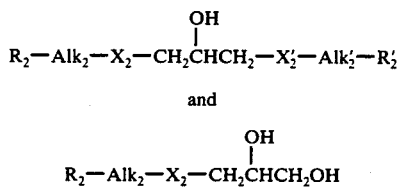

wherein
each of $R_2$ and $R_2'$ stands for hydrogen, hydroxy, hydroxyalkyl, alkoxy, alkylthio or alkylamino,
each of $Alk_2$ and $Alk_2'$ stands for alkylene which may be interrupted by —O—, —S—, or —N(Q)— wherein Q is hydrogen or a $C_1$-$C_5$ alkyl group
each of $X_2$ and $X_2'$ stands for —O—, —S—, or —N(Q)— wherein Q is as defined above, and
wherein at least one of $R_2$, $R_2'$, $X_2$, $X_2'$, $Alk_2$ and $Alk_2'$ is or comprises a thioether sulphur atom.
4. A method according to claim 1, wherein the compound corresponds to the formula:

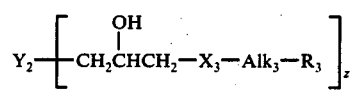

wherein:
$Y_2$ is the residue of a polyhydric alcohol containing at least 3 hydroxyl groups wherein at least 1 of the alcohol hydrogen atoms are replaced by the group between brackets,
z is an integer of at least 1,
$X_3$ is —O—, —S— or —N(Q)— wherein Q is hydrogen or a $C_1$-$C_5$ alkyl group,
$Alk_3$ is $C_1$-$C_5$ alkylene, and
$R_3$ is hydrogen, hydroxy, hydroxyalkyl, alkoxy, alkylthio, or alkylamine, and
wherein at least one of $X_3$, $Alk_3$, $R_3$ is or comprises a thioether sulphur atom.
5. A method according to claim 4, wherein in the formula z is 3 and Y is the residue of glycerol.

6. Method according to claim 1, wherein the compound is present in the developing composition.

7. Method according to claim 6, wherein the compound is used in an amount between about 50 mg and about 10 g per liter.

8. Method according to claim 1, wherein the developable silver halide has been formed by uniform re-exposure of the image-wise exposed and black-and-white developed silver halide element.

9. Method according to claim 1, wherein the photographic element is a colour element and the development is a colour development.

10. Method according to claim 9, wherein the photographic colour element has incorporated colour couplers.

11. Method according to claim 9, wherein the photographic colour element is a multicolour element comprising a blue-sensitive emulsion layer with yellow-forming colour coupler, a green-sensitized emulsion layer with magenta-forming colour coupler and a red-sensitized emulsion layer with cyan-forming colour coupler.

12. A photographic developer comprising a silver halide developing agent and a compound corresponding to the following formula and containing in its molecule at least one thioether sulphur atom linked to two carbon atoms:

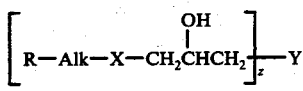

wherein:
R is hydrogen, hydroxy, hydroxyalkyl, alkoxy, alkylthio or alkylamino,
Alk is an alkylene group which may be interrupted by —O—, —S—, or —N(Q)— wherein Q is hydrogen or a $C_1$-$C_5$ alkyl group,
X is —O—, —S— or —N(Q)— wherein Q has the above meaning, and the value of z and the significance of Y are interdependent:
z being 1 for Y being hydroxy or the group —X'—Alk'—R' wherein X', Alk' and R' have the same significance as X, Alk and R,
z being 2 for Y being —O—, —S— or —N(Q)— wherein Q has the above meaning, and
z being a positive integer of at least 1 for Y being the residue of an aliphatic compound with more than one alcohol, thiol or amine function in which all or part of the alcohol-, thiol- or amine-hydrogen atoms are replaced by the group

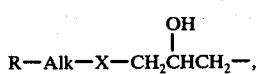

and
wherein the or at least one of the hydroxyl groups may have been converted into groups of the formula —OZA wherein Z is CO, $SO_2$ or CONH, and A is an alkyl or aryl group and wherein at least one of R, Alk, X and Y is or includes a thioether sulphur atom.

13. A photographic developer according to claim 12, wherein the compound corresponds to the formula:

wherein:
each of $Y_1$ and $Y_1'$ represents —O—, —S— or —N(Q)— wherein Q is hydrogen or a $C_1$-$C_5$ alkyl group,
n is 0 or 1,
alkylene is an alkylene group which may be interrupted by —O—, —S— or —N(Q)— wherein Q is as defined above,
each of $X_1$ and $X_1'$ represents —O—, —S— or —N(Q)— wherein Q is as defined above,
each of $Alk_1$ and $Alk_1'$ is an alkylene group which may be interrupted by —O—, —S— or —N(Q)— wherein Q is as defined above, and
each of $R_1$ and $R_1'$ stands for hydrogen, hydroxy, hydroxyalkyl, alkoxy, alkylthio or alkylamino;
and wherein at least one of $R_1$, $Alk_1$, $X_1$, $R_1'$, $Alk_1'$, $X_1'$, $Y_1$, $Y_1'$ or alkylene is or comprises a thioether sulphur atom.

14. A photographic developer according to claim 12, wherein the compound corresponds to one of the formulae:

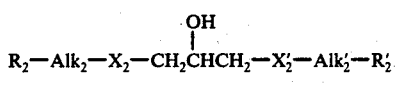

and

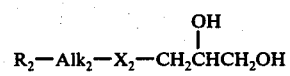

wherein
each of $R_2$ and $R_2'$ stands for hydrogen, hydroxy, hydroxyalkyl, alkoxy, alkylthio or alkylamino,
each of $Alk_2$ and $Alk_2'$ stands for alkylene which may be interrupted by —O—, —S—, or —N(Q)— wherein Q is hydrogen or a $C_1$-$C_5$ alkyl group
each of $X_2$ and $X_2'$ stands for —O—, —S—, or —N(Q)— wherein Q is as defined above, and
wherein at least one of $R_2$, $R_2'$, $X_2$, $X_2'$, $Alk_2$ and $Alk_2'$ is or comprises a thioether sulphur atom.

15. A photographic developer according to claim 12, wherein the compound corresponds to the formula:

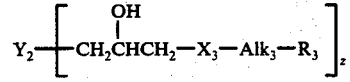

wherein:
$Y_2$ is the residue of a polyhydric alcohol containing at least 3 hydroxyl groups wherein at least 1 of the alcohol hydrogen atoms are replaced by the group between brackets,
z is an integer of at least 1,
$X_3$ is —O—, —S— or —N(Q)— wherein Q is hydrogen or a $C_1$-$C_5$ alkyl group,
$Alk_3$ is $C_1$-$C_5$ alkylene, and $R_3$ is hydrogen, hydroxy, hydroxyalkyl, alkoxy, alkylthio, or alkylamine, and wherein at least one of $X_3$, $Alk_3$, $R_3$ is or comprises a thioether sulphur atom.

16. A photographic developer according to claim 15, wherein in the formula $z$ is 3 and Y is the residue of glycerol.

17. A photographic developer according to claim 12 wherein the thioether compound is present in an amount comprised between about 50 mg and 10 g per liter.

18. A photographic developer according to claim 12, wherein the developing agent is an aromatic primary amino colour developing agent.

19. A photographic developer according to claim 18, wherein the developing agent is a p-phenylenediamine colour developing agent.

20. A photographic element containing at least one silver halide emulsion layer and a compound corresponding to the following general formula and containing in its molecule at least one thioether sulphur atom linked to two carbon atoms:

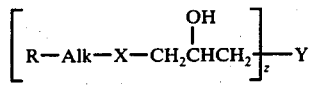

wherein:
R is hydrogen, hydroxy, hydroxyalkyl, alkoxy, alkylthio or alkylamino,
Alk is an alkylene group which may be interrupted by —O—, —S—, or —N(Q)— wherein Q is hydrogen or a $C_1$-$C_5$ alkyl group,
X is —O—, —S— or —N(Q)— wherein Q has the above meaning, and the value of $z$ and the significance of Y are interdependent:
$z$ being 1 for Y being hydroxy or the group —X'—Alk'—R' wherein X', Alk' and R' have the same significance as X, Alk and R,
$z$ being 2 for Y being —O—, —S— or —N(Q)— wherein Q has the above meaning, and
$z$ being a positive integer of at least 1 for Y being the residue of an aliphatic compound with more than one alcohol, thiol or amine function in which all or part of the alcohol-, thiol- or amine-hydrogen atoms are replaced by the group

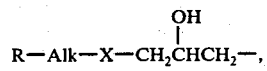

and
wherein the or at least one of the hydroxyl groups may have been converted into groups of the formula -OZA wherein Z is CO, $SO_2$ or CONH, and A is an alkyl or aryl group and wherein at least one of R, Alk, X and Y is or includes a thioether sulphur atom.

21. A photographic element according to claim 20, wherein the compound corresponds to the formula:

wherein:

each of $Y_1$ and $Y_1'$ represents —O—, —S— or —N(Q)— wherein Q is hydrogen or a $C_1$-$C_5$ alkyl group,
$n$ is 0 or 1,
alkylene is an alkylene group which may be interrupted by —O—, —S— or —N(Q)— wherein Q is as defined above,
each of $X_1$ and $X_1'$ represents —O—, —S— or —N(Q)— wherein Q is as defined above,
each of $Alk_1$ and $Alk_1'$ is an alkylene group which may be interrupted by —O—, —S— or —N(Q)— wherein Q is as defined above, and
each of $R_1$ and $R_1'$ stands for hydrogen, hydroxy, hydroxyalkyl, alkoxy, alkylthio or alkylamino;
and wherein at least one of $R_1$, $Alk_1$, $X_1$, $R_1'$, $Alk_1'$, $X_1'$, $Y_1$, $Y_1'$ or alkylene is or comprises a thioether sulphur atom.

22. A photographic element according to claim 20, wherein the compound corresponds to one of the formulae:

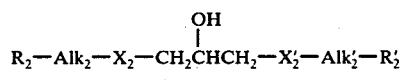

and

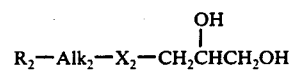

wherein
each of $R_2$ and $R_2'$ stands for hydrogen, hydroxy, hydroxyalkyl, alkoxy, alkylthio or alkylamino,
each of $Alk_2$ and $Alk_2'$ stands for alkylene which may be interrupted by —O—, —S—, or —N(Q)— wherein Q is hydrogen or a $C_1$-$C_5$ alkyl group
each of $X_2$ and $X_2'$ stands for —O—, —S—, or —N(Q)— wherein Q is as defined above, and
wherein at least one of $R_2$, $R_2'$, $X_2$, $X_2'$, $Alk_2$ and $Alk_2'$ is or comprises a thioether sulphur atom.

23. A photographic element according to claim 20, wherein the compound corresponds to the formula:

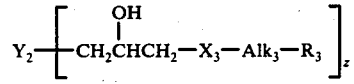

wherein:
$Y_2$ is residue of a polyhydric alcohol containing at least 3 hydroxyl groups wherein at least 1 of the alcohol hydrogen atoms are replaced by the group between brackets,
$z$ is an integer of at least 1,
$X_3$ is —O—, —S— or —N(Q)— wherein Q is hydrogen or a $C_1$-$C_5$ alkyl group,
$Alk_3$ is $C_1$-$C_5$ alkylene, and
$R_3$ is hydrogen, hydroxy, hydroxyalkyl, alkoxy, alkylthio, or alkylamine, and
wherein at least one of $X_3$, $Alk_3$, $R_3$ is or comprises a thioether sulphur atom.

24. A photographic element according to claim 23, wherein in the formula $z$ is 3 and Y is the residue of glycerol.

* * * * *